United States Patent [19]
Kraska et al.

[11] 4,089,226
[45] May 16, 1978

[54] SYSTEM FOR RESIDUAL TIRE LIFE PREDICTION BY ULTRASOUND

[75] Inventors: Irvin R. Kraska, Lansing; John Stark, Bartlett; Wieslaw L. Lichodziejewski, Schaumburg, all of Ill.

[73] Assignee: Gard, Inc., Niles, Ill.

[21] Appl. No.: 776,273

[22] Filed: Mar. 10, 1977

[51] Int. Cl.² .................................................. G01N 29/04
[52] U.S. Cl. .......................................... 73/614; 73/146; 73/901
[58] Field of Search .................. 73/67.5 R, 67.6, 67.7, 73/67.8 R, 67.8 S, 67.9

[56] References Cited

U.S. PATENT DOCUMENTS

| | | | |
|---|---|---|---|
| 2,378,237 | 6/1945 | Morris | 73/146 X |
| 3,148,535 | 9/1964 | Lemelson | 73/146 X |

Primary Examiner—Herbert Goldstein
Attorney, Agent, or Firm—Claron N. White

[57] ABSTRACT

A residual tire life prediction system uses a clock to trigger a bang generator that provides pulses of electrical energy to a pulse-echo transducer. The transducer converts pulses of electrical energy to pulses of ultrasonic vibration. The transducer is located on the tread of a steel belted tire to transmit pulses of ultrasonic energy into the tire and to receive reflected ultrasonic energy from plies of the tire casing. The transducer converts the reflected ultrasonic energy to provide bursts of electrical signals. The transducer is connected to a time varying gain control circuit that has its output connected via a full-wave rectifier to a first gate and to an input of a voltage level detector. The clock is also connected to a first time-delay circuit that is operative after a delay, subsequent to the pulse of the bang generator, to enable a second gate, connected to the output of the voltage level detector, that provides a signal, when it receives the signal based on the reflection from the outer steel belt, to a second time-delay circuit that provides an enable signal at its output after a predetermined delay for a predetermined period of time to the first gate to open it for passage of signals from the rectifier to a peak sensing device that provides an output signal to a digital panel meter for display of the value of the maximum amplitude passing through the first gate.

19 Claims, 6 Drawing Figures

SYSTEM FOR RESIDUAL TIRE LIFE PREDICTION BY ULTRASOUND

CROSS-REFERENCE TO RELATED APPLICATION

Copending U.S. patent application Ser. No. 667,417, having the same title as the present patent application was filed on Mar. 16, 1976 by six applicants. Two of the applicants are two of the three applicants of the present patent application. Those two applicants and two other applicants have assigned their undivided interest in the title to the invention and application to the assignee of the present patent application.

BACKGROUND OF THE INVENTION (1) Field of the Invention

There are many nondestructive inspection methods presently being applied to tires. Most use X-radiography, infrared, holography and ultrasonic methods.

This invention relates to the testing of steel belted tires to determine their condition using nondestructive testing by a pulse-echo type of reflection pulse ultrasonic system.

(2) Description of the Prior Art

Various pulse ultrasonic systems have been developed for the inspection of tires. Known U.S. patents in this field are U.S. Pat. Nos. 2,378,237; 3,148,535; 3,336,794; 3,815,407 and 3,882,717.

The systems of the first two patents and the fourth patent are described in said copending patent application along with the description of the system used by Australian investigators and a system using an ultrasonic test instrument for examining tires with a cathode ray tube for a video display of the test data. That description is hereby incorporated by reference. The third and fifth patents mentioned above disclosed systems that use a through transmission type of ultrasonic testing of tires but that type of ultrasonic examination is not suitable to determine the condition of plies of a casing of a tire.

SUMMARY OF THE INVENTION

A tire has a casing that has a number of plies and each ply has cords in a rubber matrix. A tire may be unbelted or belted. The belted tires are normally bias or radial. The belted tire can contain belts of steel or textile cords. The system of the present invention is useful to determine the residual life of a steel belted tire whether it is a steel belted bias tire or a steel belted radial tire.

A tire during its life degrades due to age, use, and mileage interactions. The prime loading-carrying structure, namely, the plies, loosen up (i.e., the cords in the plies become gradually more debonded from the surrounding rubber matrix). This degradation will reach a state where the plies become separated internally and with further use tread will separate from the tire at this degraded ply separation area, causing hazardous vehicle operation. Another cause of ply separation is a manufacturing induced effect. This is not degradation induced. Manufacturing separations are related to tire degradation; however, for most cases in a new, or slightly used, tight undegraded tire, manufactured-in separations will either not grow or grow in a slow controlled manner, but in a used, weakened, degraded casing such separations will grow quickly and thus potentially cause tire failure.

The system of the invention of said copending patent application predicts residual tire life (by sensing ply degradation) and finds both degradiation-induced and manufactured-in separations by a reflection pulse ultrasonic system. The system of that invention was found to be useful to make this prediction with respect to textile ply tires and can use either a pitch-catch type or preferably a pulse-echo type of reflection pulse ultrasonic method. The system of that invention is useful to examine portions of the casing of the tire to provide information with respect to the condition of plies of the casing. The signal processing means of that system in one of its simplest forms of apparatus provides a signal, preferably as a digital readout, representing signals based on reflected energy and thus representing the condition of at least the outer plies of the casing. That signal can be read and compared with the signal that the processing means would provide in the examination of a properly manufactured new, unused tire.

The pulse ultrasonic reflection system of the invention of that copending patent application comprises: imparting pulses of ultrasonic energy into an area of a tire in a manner to provide pulses of reflected acoustic energy so that each reflected pulse includes reflected ultrasonic energy from the plies of the casing of the tire; converting the pulses of reflected acoustic energy to pulses of electrical signals; amplifying the electrical signals; processing the pulses of amplified electrical signals to provide information with respect to the amplitude of those amplified electrical signals based on the reflected acoustic energy from at least one of the plies of the casing; determining the difference between that information and information obtainable by the same processing of amplified signals from acoustic energy reflected from the same ply or plies of an unused, new tire that is the same type and that has a satisfactory ply construction and has a satisfactory bonding of the cords to the rubber matrix of the tire casing; and predicting from that difference the extent of circumferential degradation and thus the residual life of the tire being tested by the system.

In that system the processing of the amplified electrical signals based on the reflected acoustic energy from at least one of the plies of the casing is able to provide information because the system provides a time gating of electrical signals so that the passed signals do not include the electrical signal that is the pulse from the bang generator or that is the result of reflected acoustic energy from the outer surface of the tread of the tire.

Furthermore, in that system the time gating for the signals is provided by gate means having a gate that is opened after a predetermined period of time following each pulse from the bang generator that provides high-frequency electrical energy to a transducer that imparts each pulse of ultrasonic energy to the tire. The gate when opened passes the amplified signals to the processing means.

In one embodiment of that system these ply-reflected signals are processed by peak sensing means that provides an output signal indicative of the maximum amplitude of the time-gated signals and the output of the peak sensing means is illustratively an input to a digital voltmeter and a level sensing means. This signal to the level sensing means is compared with a reference voltage. When the voltage from the peak sensing means is a greater value than that of the reference voltage, there is a signal at the output of the level sensing means. That signal turns on a light indicating the tire should be rejected. If the light is lit, a signal from the level sensing means is a blanking signal to the digital voltmeter in a preferred construction.

In a modification of this embodiment of that system, the level sensing means is replaced by a ratio sensing means that receives the signal from the peak sensing means as well as receiving a voltage signal from a second peak sensing means that is also present. The second peak sensing means is connected to a second gate of the gate means in this modified construction. That gate is opened after a predetermined delay after detection of the first echo by other circuitry, in the gate means. Thus there are two timed-gate operations, both being opened after a delay. This permits the determination of the maximum amplitude of signals to the two peak sensing means and their ratios are determined by the ratio sensing means. If the ratio exceeds a predetermined value, the ratio sensing means provides an output signal to turn on the light and, if desired, to blank the digital voltmeter. This modification is an examination of the condition of two different groups of plies of the casing of the tire. It is useful to discriminate between ply separations and degradation (i.e. cord loosening). It can provide this determination even though the value displayed by the digital voltmeter might have been the same in both cases.

Various other illustrative processing means are described as other embodiments of the system of said copending patent application. These include the use of an integrator for inspection of a stationary tire and the use of summing means, i.e., the combination of a voltage-to-frequency converter and a digital counter, for inspection of a rotated tire.

The system of the present invention is useful to predict residual life of a steel belted tire by a pulse-echo type of reflection ultrasound examination. This system provides, for each pulse from the bang generator, a time gating of the signals passed from the amplifier circuit, described below, to the processing means but only after other circuitry of the system, after a delay subsequent to the pulse from the bang generator, has identified an amplified signal as being the signal based on the reflected ultrasonic energy from the outer steel belt of the casing of the tire and then has initiated, after a predetermined delay, the processing of subsequent signals. As a result, the examination is performed only for plies inwardly of the outer steel belt or inwardly of a couple of outer steel belts. The initiation of a processing of amplified reflected signals is based not merely on a time delay following the signal from the clock; rather there is a combination of such delay and a delay initiated by the amplified signal due to reflected acoustic energy from the outer belt of the casing of the tire.

More specifically the system of the present invention comprises a pulse-echo transducer, a clock, a first time-delay relay circuit and a bang generator. The clock provides periodic voltage signals at its output to trigger the first time-delay circuit that provides a signal, after a predetermined delay, to the bang generator. The generator (which is a pulser) thereby provides pulses of high-frequency electrical energy to the transducer that converts them to pulses of ultrasonic vibration. In the use of the system the transducer is placed against the tread of a tire, preferably at the midline, to impart the pulses of ultrasonic energy into the tire toward the plies of the casing of the tire. The transducer receives the bursts of ultrasonic energy reflected by the plies of the tire and converts this energy to bursts of voltage signals.

The system includes an amplifier circuit with an time varying gain control circuit that has its input connected to the transducer. The time varying gain control circuit is constructed to provide the amplifier circuit with an increase in gain of amplification with time following each clock signal. The amplifier circuit has its output connected, via a full-wave rectifier, to a first gate and to a voltage level indicator which compares the rectified amplified signals with a reference voltage so that there is only an output signal from the indicator when the amplified voltage signal exceeds a predetermined voltage level. The clock is also connected to a second time-delay circuit. Each clock pulse, that triggers the first time-delay circuit, triggers a second time-delay circuit that, for a predetermined period of time, provides a disable signal, i.e., an inhibit signal, to one input of a second gate having its other input connected to the output of the voltage level indicator. That disable signal closes the second gate. When the first signal is at the output of the voltage level indicator after the second gate is opened, the signal is passed by the second gate to trigger a third time-delay circuit that, after a predetermined delay, provides an enable signal at its output for a predetermined period of time. That output of the third time-delay circuit is connected to the first gate. This enable signal from the third time-delay circuit opens the first gate to pass the rectified amplified signals from the full-wave rectifier.

The output of the first gate is connected to signal processing means having the construction to provide a voltage signal, representing the condition of plies, as described in said copending patent application. Preferably the processing means includes peak sensing means and a digital panel meter. The output of the first gate is connected to the peak sensing means and its output is connected to the digital panel meter. It is especially preferred that the output of the peak sensing means is connected also to a comparator that compares the voltage signals to a reference voltage. If there is a higher voltage of the signal from the peak sensing means, there is an output signal from the comparator. That output is connected to a defect indicator and preferably, also to the digital panel meter to provide a blanking signal to that meter. Thus the signal from the comparator turns on a light and blanks the meter.

In a preferred aspect of the system of the invention, the system includes a capability of examining textile tires, i.e. tires that are all textile cord in a rubber matrix. This system is a universal system that can alternatively examine four types of tires, namely, passenger or truck steel belted tires or passenger or truck textile tires. In this case the second gate is a part of a gate circuit that includes other gates and the third time-delay circuit is constructed to provide alternative periods of delay before enabling the first gate and different periods of time during which the first gate is enabled. In this aspect of the system a rotary switch having a number of decks is used. Four positions of the switch are used as four modes of operation based on the four types of tires mentioned above. Each deck has two halves with each half providing four switch positions at which its moving contact engages four fixed contacts.

One of these decks has one-half used to switch between two alternative operations of the gate circuit that includes the second gate. One operation is used when the tire to be tested is a textile tire. The other is used when the tire is a steel belted tire. Thus two fixed contacts are connected to each other to provide the same operation of the gate circuit when either is contacted by the moving contact. The other two fixed contacts are connected to each other to provide the other operation of the gate circuit when either is contacted by the moving contact and to inhibit the first-mentioned operation, namely the operation used for testing other than passenger or truck textile tires.

One half each of the second deck and the third deck is used to provide alternative external timing components for the third time-delay circuit that controls the start of the enabling of the first gate and the period of time that that gate is enabled to pass signals from the full-wave rectifier to the peak sensing means.

This instrument, that has capability of testing textile tires as well as steel belted tires, is constructed to provide a different frequency at which the pulse-echo transducer rings when it is pulsed by the bang generator. For the testing of steel belted tires, whether passenger tires or truck tires, it is preferred to use a pulse-echo transducer having a crystal that rings at a frequency of about 750 kHz. This is satisfactory also for the testing of truck textile tires. Some passenger textile tires have an inner-liner that provides to the first gate a voltage signal that has a higher amplitude than the amplitudes resulting from the reflected ultrasonic energy produced by the textile plies of the casing of such tires. This would result in a display on the digital panel meter of a value higher than that due to plies of the tire. It was found that this could be avoided to provide a true indication of the condition of the plies of the tire by tuning the transducer to ring at a higher frequency, illustratively a frequency of about 1,000 kHz. To do this a RF autotransformer is connected in parallel with the transducer. The connection between the bang generator, transducer and the amplifier circuit is provided by the de-energized relay. When the relay is energized, the RF autotransformer input is connected to the bang generator and the transducer serving as a tuner and a step up transformer into the amplifier circuit. The relay is energized when the rotary switch is at the position for the mode of testing a passenger textile tire so that the moving contact of the second half of first deck contacts a fixed contact connected to a voltage source. For the testing of the other three types of tires that switch is at one of the other three modes or positions at which that moving contact connects one of the three other fixed contacts. All three are connected to ground so that the relay is not energized.

Because the system for testing the passenger textile tire uses the different frequency for which the transducer rings and because the attenuation of the acoustic energy is different at this higher frequency, the second half of the third and fourth decks are used to provide two alternative operations of an amplitude and slope control that determine the initial gain and the slope or rate of gain of the time varying gain control circuit. These portions of the third and fourth decks are connected to the amplitude and slope control so that there is a higher initial gain and a steeper slope for the gain with time when these switches of those decks of the rotary switch are at a position that is the mode for testing a passenger textile tire.

Two fixed contacts of the first half of the first deck of the rotary switch are connected to each other and to the gate circuit to enable that circuit for steel belted tire testing, when either fixed contact is engaged by the moving contact connected to ground. When the moving contact engages the other fixed contacts, the gate circuit is inhibited for steel belted tire testing but is enabled for textile tire testing. As a result, the gate circuit functions in two different manners to signal the time-delay circuit for the enabling the first gate. In the operation of the gate circuit for textile tire testing, the voltage level indicator is not used. A gate of the gate circuit is not dependent upon an output signal from the voltage level indicator to provide a signal to the third time-delay because that gate provides that signal when an additional gate, that is enabled by the position of the rotary switch in the passenger textile tire mode, is provided the clock pulse.

DETAILED DESCRIPTION

Figure 1:
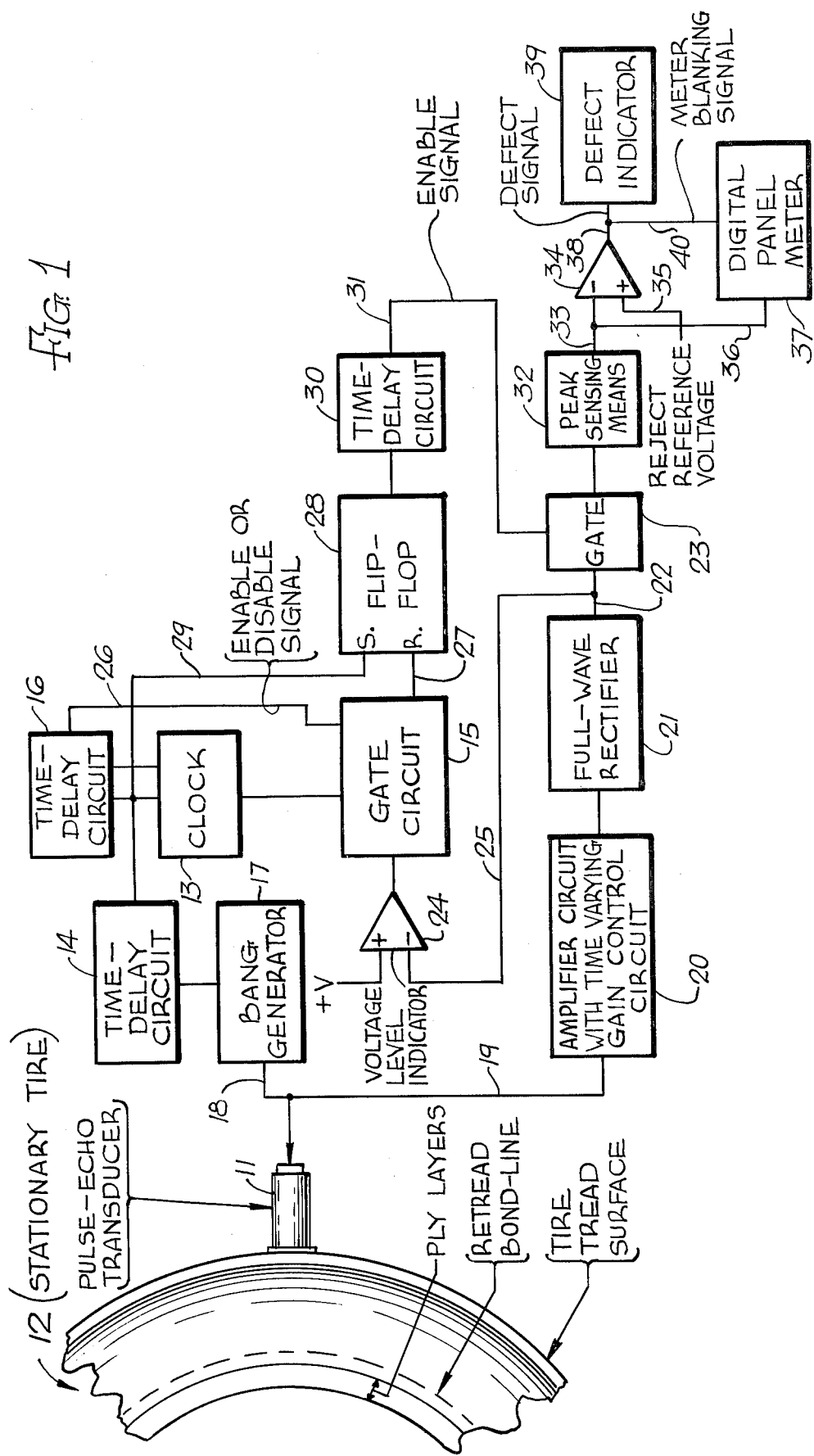
FIG. 1 is a schematic electrical block diagram of the system of the invention for the testing of steel belted tires.

Referring to FIG. 1, a pulse-echo transducer 11 is, in use, placed against the midline of the thread of a tire 12. A clock 13, illustratively operating at about 3 kHz, provides at its $\overline{Q}$ output low-level signals through an inverter (not shown) to a time-delay circuit 14 and low-level signals to a gate circuit 15 and to a set input of a flip-flop mentioned below. The $\overline{Q}$ output of clock 13 is connected to the time-delay circuit 16. The time-delay circuit 14, after a delay following the triggering of clock 13, provides a signal to a bang generator 17 that provides a pulse signal to transducer 11 by a line 18. The line 18 is connected also to a line 19 that is connected to an input of an amplifier circuit with a preamplifier, a time varying gain control circuit and a final amplifier. The amplifier circuit 20 provides an amplified signal, having increased gain with time, to a full-wave rectifier 21 that has its output connected by a line 22 to an input of a gate 23. A voltage level indicator 24 has one of its inputs connected to line 25 and thus to rectifier 21. The other input of voltage level indicator 24 is connected to a reference voltage source.

The time-delay circuit 16 illustratively times out about 5 microseconds after time-delay circuit 14 times out. Illustratively time-delay circuit 16 is a monostable multivibrator. When time-delay circuit 16 is triggered by a pulse from clock 13, it provides a signal at its $\overline{Q}$ output via a line 26 to gate circuit 15. This signal on line 26 during the timing out of time-delay circuit 16 is a disable signal, so that the output of gate circuit 15 does not provide a signal on the line 27 to reset a RS-type flip-flop 28 until time-delay circuit 16 times out, even though there may be output signals from voltage level indicator 24.

When time-delay circuit 16 times out, its $\overline{Q}$ output voltage signal changes so that the signal on line 26 is then an enable signal to gate circuit 15. Thereafter any output signal from voltage level indicator 24 will be passed through gate circuit 15 to reset flip-flop 28. The time-delay of circuit 16 is such that it will not provide the enable signal to gate circuit 15 until after a predetermined period of time subsequent to the pulse from bang generator 17 to transducer 11. The reference voltage provided to voltage level indicator 24 is sufficiently great so that it will require a substantial reflected ultrasonic energy to transducer 11 to provide a sufficient amplitude of the signal on line 25 to have an output signal to gate circuit 15 from indicator 24. This occurs and is gated only when the ultrasonic energy is reflected from the outermost steel belt of tire 12.

The clock 13 has its output, that triggers time-delay circuits 14 and 16, connected by a line 29 to the set input of flip-flop 28 so that it is set at the end of each pulse from clock 13.

Figure 2:
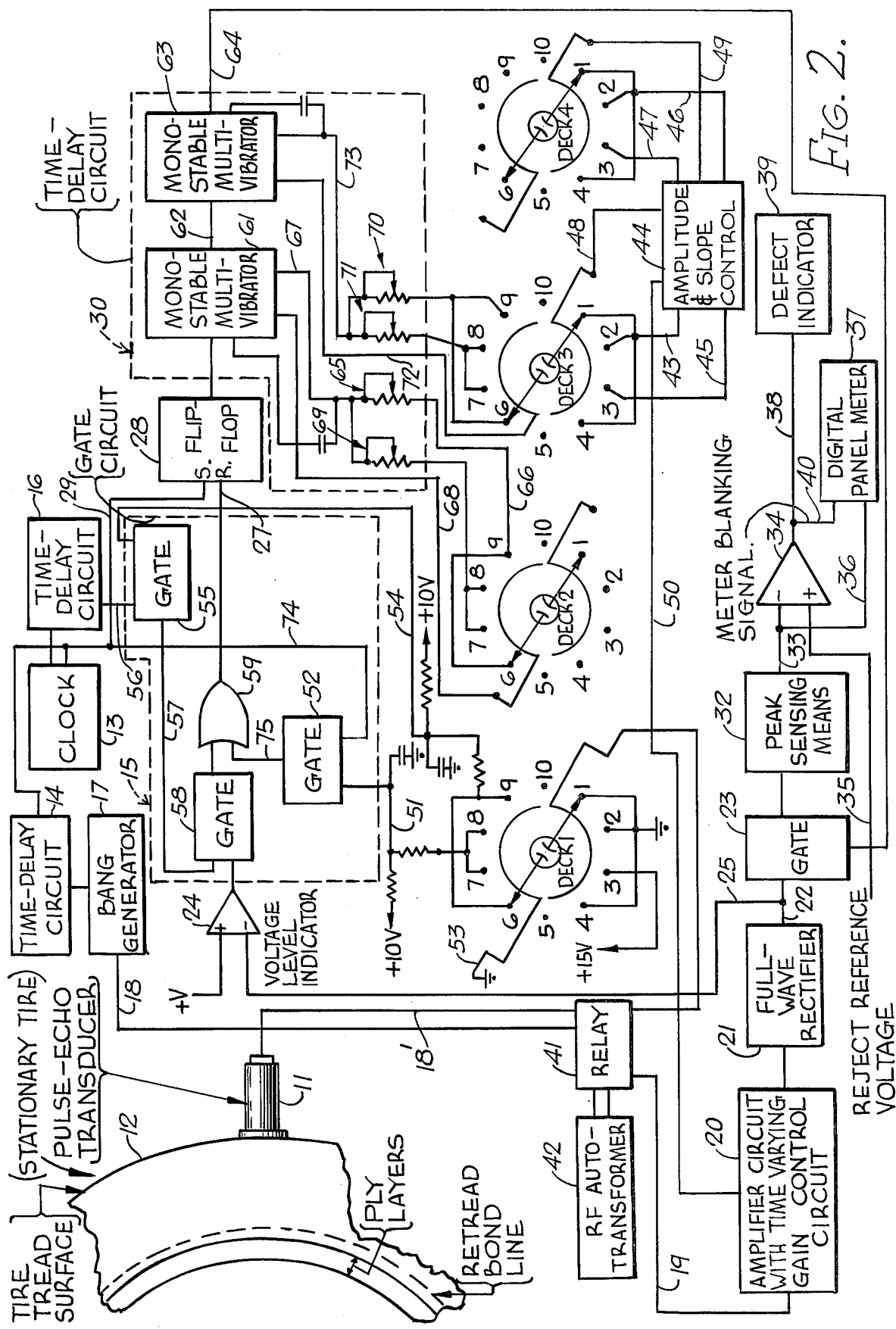
FIG. 2 is a schematic electrical drawing of the preferred embodiment of the system of the invention capable of alternatively testing passenger steel belted tires, truck steel belted tires, passenger textile tires, or truck textile tires.

One of the outputs to flip-flop 28 is connected by a line (not numbered) to a time-delay circuit 30 so that it is triggered when flip-flop 28 is reset by the signal passing from voltage level indicator 24 through gate circuit 15. The time-delay circuit 30 is constructed illustratively with two monostable multivibrators (arranged relative to flip-flop 28 as shown in FIG. 2). The first monostable multivibrator is triggered when flip-flop 28 is reset and when the multivibrator times out, illustratively after about 5 microseconds, it provides a signal at its output that triggers the second monostable multivibrator. When the second monostable multivibrator is triggered, its output provides an enable signal to a line 31 for a period of time, for example, about 4.4 microseconds. The line 31 is connected to another input of gate 23 and the enable signal on line 31 opens gate 23 to pass signals on line 22 from rectifier 21 via a line (not numbered) to a peak sensing means 32. Because of the timing delays mentioned above gate 23 is open to pass signals based on reflection from plies other than the first one or several outer steel belts of the casing of the tire.

The output of peak sensing means 32 is connected by a line 33 to one input of a comparator 34 where it is compared with a reject reference voltage provided by a line 35. A line 36 is connected to line 33 and thus to the output of peak sensing means 32. The line 36 is connected to an input of a digital panel meter 37 that provides a digital display representative of the voltage signal at the output of peak sensing means 32 and thus indicates the condition of tire's inner plies and thereby the residual tire life. Illustratively, digital panel meter 37 is adjusted to display a numerical value of 20 for a new, unused steel belted tire that provides a particular voltage at the output of peak sensing means 32. With service use there will be a degradation of inner plies of the casing. As a result the reflected ultrasonic energy from these inner plies of the tire will provide output signals from peak sensing means 32 during the time that gate 23 is enabled that are displayed by digital panel meter 37 as digital numbers lower than 20.

In the event that the tire has changed with service to the extent that at least one of the inner plies provides a signal from peak sensing means 32 that the ply or plies have degraded beyond the condition of circumferential cord loosening to the condition of circumferential cord separation, the reflected ultrasonic energy will be sufficiently great that the voltage signal to digital panel meter 37 may be greater than 20, e.g., 28 or greater. Comparator 34 is adjusted so that it will provide an output signal, in the event of cord separation, to a line 38 connecting comparator 34 to a defect indicator 39. A light (not shown) of indicator 39 is lit by this signal from comparator 34. A line 40 connects line 38 and thus comparator 34 to digital panel meter 37. The line 40 is connected to a blanking input of meter 37 so that its display is blanked by the signal on line 40 from comparator 34.

In FIG. 2 the various components that are common with those shown in the embodiment of the system in FIG. 1 generally have the same numbers. The embodiment shown in FIG. 2 includes a number of other components and the construction of gate circuit 15 and time-delay circuit 30 are more complex.

Figure 3A:
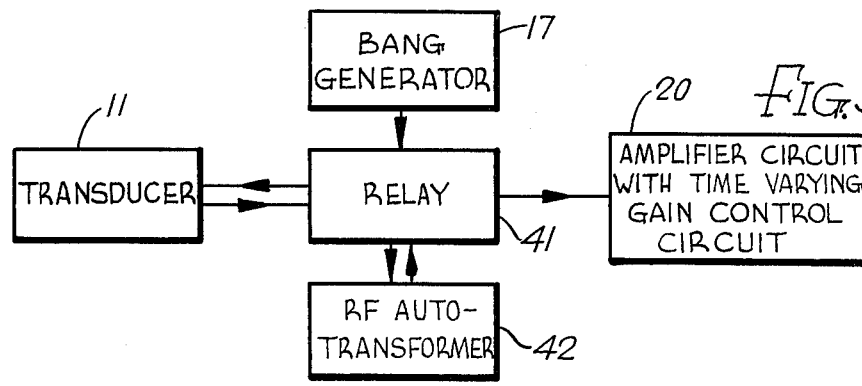
FIGS. 3A, 3B and 3C are schematic drawings relating to the alternative testing of passenger textile tires or any of the other three types of tires mentioned above.
Figure 3B:
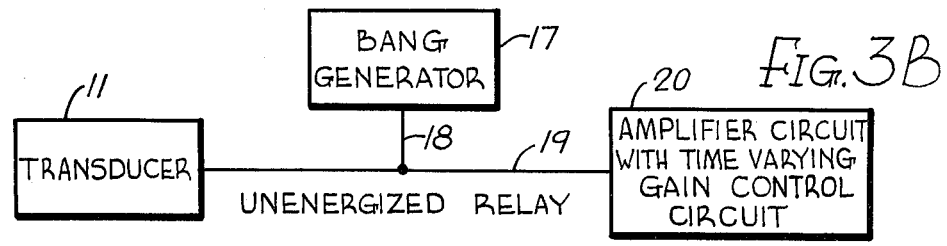
Figure 3C:
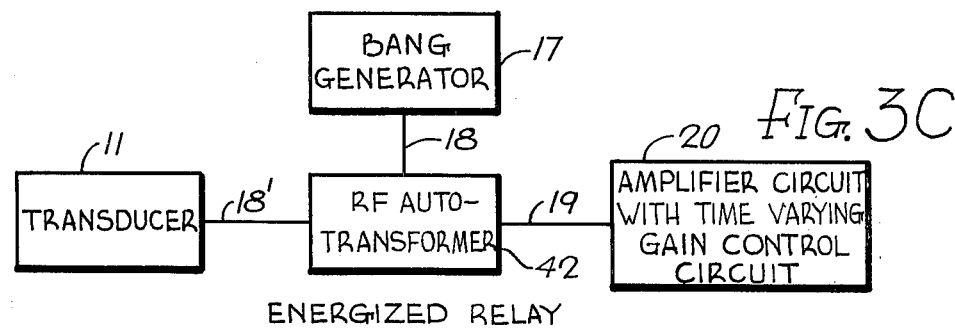

The embodiment of FIG. 2 includes a relay 41 and a RF autotransformer 42 that is wound on a toroid core. The relay 41 is present to increase the frequency at which the crystal of transducer 11 rings when the tire to be inspected is a passenger textile tire. When the tire is one of the other three types the connection of bang generator 17 to transducer 11 and to amplifier circuit 20 is the same as shown in FIG. 1. When relay 41 is energized, RF autotransformer 42 is connected to transducer 11 and bang generator 17 so that the crystal of transducer 11 rings at a higher frequency and also RF autotransformer 42 is a step up transformer so that a larger signal is transmitted to amplifier circuit 20 via line 19. The functional relationship between these various components is shown in FIG. 3A and the two modes of operation, i.e., with and without the energization of relay 41 are shown in FIGS. 3B and 3C.

To provide the capability of testing the four types of tires, the embodiment of the system of the invention of FIG. 2 includes a rotary switch having a number of decks, of which four decks are used. These decks are identified as decks 1 through 4. Each deck has two switches that move together and each deck has two moving contacts. Each moving contact can be moved to contact its own set of fixed contacts. In the particular rotary switch, that was used, there were ten contacts but only eight contacts are used for each switch of the deck. They are identified as fixed contacts 1 through 4 for one switch and 6 through 9 for the other switch of the deck. The fixed contacts 1 through 4 of deck 2 and 6 through 9 of deck 4 are not used.

Fixed contacts 1, 2 and 4 of deck 1 are connected to ground while fixed contact 3 is connected to a +15V source to provide selectively a signal to a line (not numbered) connected to relay 41 or to connect relay 41 to ground. Fixed contacts 1, 2, and 4 of deck 3 are connected to one another and by a line 43 to one terminal of an amplitude and slope control 44 while fixed contact 3 of deck 3 is connected by a line 45 to a second terminal of amplitude and slope control 44. Similarly fixed contacts 1, 2 and 4 of deck 4 are connected to one another and connected by a line 46 to a third terminal of amplitude and slope control 44 while fixed contact 3 of deck 4 is connected by a line 47 to a fourth terminal of amplitude and slope control 44. The moving contacts of decks 3 and 4 that illustratively connect with contacts 1 through 4 of these decks are connected by lines 48 and 49, respectively, to still other terminals of amplitude and slope control 44.

The amplitude and slope control 44 is constructed with two sets of trimmers. The two trimmers of the first set are connected to lines 43 and 45 while the other 2 sets of trimmers are connected to lines 46 and 47. This part of deck 3 provides alternative gain control amplitude adjustment in which the initial gain, when contact 3 of deck 3 is contacted by the moving contact, is greater than when the switch is in one of the three other positions. This is because of the different adjustment of the two trimmers connected to lines 43 and 45. Similarly the different slope adjustment by the other set of trimmers of amplitude and slope control 44 is provided when the moving contact of deck 4 contacts either fixed contact 3 or one of fixed contacts 1, 2 and 4. This selection of slope adjustment by use of one or the other trimmer provides alternative slopes of the gain control of amplifier circuit 20. The output of amplitude and slope control 44 is connected by a line 50 to amplifier circuit 20. The trimmers connected to lines 46 and 47 are adjusted so the slope of gain control output voltage to amplifier circuit 20 is steeper. This is because a passenger textile tire is tested with the rotary switch in the mode in which the moving contact of decks 3 and 4 contact fixed contact 3 to provide the operation of control 44 with the higher initial gain and steeper slope than is the case when the rotary switch is at any of the other three modes.

In the case of the other half of decks 1 through 3 in which their contacts 6 through 9 are used, contacts 7 and 8 of a deck are connected to each other and contacts 6 and 9 of a deck are connected to each other.

The connecting line between contacts 7 and 8 of deck 1 are connected by a resistor (not numbered) to a line 51 that is connected to an input of a gate 52, that is illustratively a NOR gate. The line 51 is connected through a resistor (not numbered) to a 10V source and line 51 is also connected through a capacitor (not numbered) to ground. The moving contact that contacts selectively fixed contacts 6 through 9 of deck 1 is connected to ground by a line 53.

Similarly fixed contacts 6 and 9 are connected through a resistor (not numbered) to a line 54 that is connected to an enable input of a gate 55 that has its other input connected by a line 56 to an output of time-delay circuit 16. In this illustration gate 55 is an OR gate that functions as an AND gate in negative logic. Accordingly, the signals on lines 54 and 56 must be low-level voltage signals to provide a low-level signal to a line 57 connecting the output of gate 55 to one input of a gate 58 that illustratively is a NOR gate that functions as a NAND gate if negative logic. Thus line 54 enables gate 55 whenever it is connected to ground by one of contacts 6 and 9 that is the case for the two positions of the rotary switch for testing passenger or truck steel belted tires; however, when neither contact 6 or contact 9 of deck 1 is connected to ground, a high-level inhibit voltage signal is provided via line 54 to that input of gate 55. This occurs when the rotary switch is positioned for textile tire inspection, i.e., so that either contact 7 or contact 8 of deck 1 is connected to ground.

The other input of gate 58 is connected to the output of voltage level indicator 24 by a line (not numbered). Until time-delay circuit 16 has timed out there is an inhibit high-level voltage signal on line 57 to gate 58. There is a low-level voltage signal on line 54 to gate 55. When circuit 16 times out, it provides a low-level voltage signal via line 56 to gate 55. Because there is a low-level voltage signal on line 54, a low-level enable voltage signal is provided by line 57 to gate 58 so that it now can pass low-level signals from indicator 24. This provides high-level signals to one input of an OR gate 59 that passes the signal by line 27 to the reset input of flip-flop 28 thereby providing a high-level voltage signal at its $\overline{Q}$ output to trigger a monostable multivibrator 61 of time-delay circuit 30 connected to that output of flip-flop 28. The $\overline{Q}$ output of multivibrator 61 is connected by a line 62 to a monostable multivibrator 63 also of time-delay circuit 30. When multivibrator 61 times out its output changes to a high-level voltage signal to provide a triggering of multivibrator 63 that provides a low-level enable voltage signal from its $\overline{Q}$ output via a line 64 to an input of gate 23. By this construction, gate 23, is enabled to pass signals from rectifier 21 to peak sensing means 32, after a delay provided by multivibrator 61, for the period of time that the enable signal on line 64 keeps gate 23 open. Of course the operation of multivibrators 61 and 63, when testing steel belted tires, are delayed until flip-flop 28 is reset by the first signal passed from indicator 24 to flip-flop 28 after the delay provided by time-delay circuit 16.

For the modes that are the two positions of the rotary switch for the inspection of passenger or truck steel belted tires, the time period for multivibrator 61 is determined by an external timing circuit including a trimmer generally indicated at 65 connected to fixed contacts 6 and 9 or deck 2 by a line 66 and to a terminal of multivibrator 61 by a line 67. Another terminal of multivibrator 61 is connected to a capacitor (not numbered) that is connected to line 67. In these positions of the rotary switch, contact 6 or contact 9 is connected by the moving contact to a line 68 that is connected to another terminal of multivibrator 61 to complete the circuitry for the external timing control for multivibrator 61. The trimmer 65 is adjusted illustratively so that multivibrator 61 times out after about 5 microseconds and then triggers multivibrator 63.

The contacts 7 and 8 are connected to line 67 via a trimmer generally indicated at 69 to provide the alternative timing operation of multivibrator 61. In that case the moving contact of deck 2 contacts either contact 7 or contact 8 of deck 2 for an inspection of truck textile tires or passenger textile tires, respectively. The trimmer 69 is adjusted to provide a timing circuit for multivibrator 61 so that it times out illustratively about 8.7 microseconds after main bang generator 17 fires.

Similarly multivibrator 63 is provided with an external timing circuit that selectively, by rotary switch position, uses a trimmer generally indicated at 70 connected to contacts 6 and 9 of deck 3, when testing steel belted truck or steel belted passenger tires or uses a trimmer generally indicated at 71 connected to contacts 7 and 8 of deck 3, when testing truck and passenger textile tires. The moving contact of deck 3 that contacts selectively contacts 6 through 9 is connected by a line 72 to a terminal of multivibrator 63 while trimmers 70 and 71 are connected by a line 73 to another terminal of multivibrator 63. The line 73 is also connected to a capacitor that is connected to a third terminal of multivibrator 63.

The trimmer 70 is adjusted illustratively to provide a timing out of multivibrator 63 after about 4.4 microseconds. This is the period of time during which, for the testing of steel belted tires, peak sensing means can receive signals from rectifier 21 because gate 23 is during that time enabled by the output signal from multivibrator 63. For the testing of textile tires, either truck or passenger tires, contact 8 or contact 7 is contacted by the moving contact to utilize trimmer 71 instead of trimmer 70. In that case illustratively trimmer 71 is adjusted so that multivibrator 63 times out after about 37 microseconds. During the period of the operation of multivibrator 63, i.e., until it times out, signals are received by peak sensing means 32 from rectifier 21.

When the moving contact of deck 1 that can be positioned to contact one of contacts 6 through 9 of deck 1 is positioned to contact either fixed contact 6 or fixed contact 9 for a testing mode for steel belted tires, neither fixed contact 7 nor fixed contact 8 is connected to ground. Thus the 10V source provides a high voltage signal to one input of gate 52. The other input of gate 52 is connected by a line 74 to line 29 that connects the Q output of clock 13 to the set input of flip-flop 28 so that both are provided with the low-level voltage signal from clock 13. The output of gate 52 is connected by a line 75 to a second input of OR gate 59. In view of the high-level voltage signal on line 51, when testing steel belted tires, a low-level signal is provided by line 75 to gate 59. Under this condition, for either of these positions of the rotary switch, gate 59 provides a reset signal to flip-flop 28 only when gate 58 is enabled, by a low-level voltage signal from gate 55, to pass a signal from indicator 24. This occurs only after time-delay circuit 16 times out. The line 54 is connected by fixed contact 6 or fixed contact 9 to ground so that it provides a low-level voltage signal to gate 55; otherwise the timing out of circuit 16, to provide a low-level voltage signal, would not provide the enabling of gate 58.

When testing a textile tire, line 51 is connected by deck 1 to ground. Until clock 13 provides the low-level voltage signal via line 74 to gate 52, there are two low-level voltage signals at the inputs of NOR gate 52. As a result there is a high-level signal via line 75 to gate 59 that then provides a high-level voltage signal via line 60 to the reset input of flip-flop 28. This initiates the automatic operation of multivibrator 61 and then multivibrator 64 to open gate 23 after a period of delay and then keep it open for a predetermined period of time.

At the end of the low-level voltage signal at the Q output of clock 13, the signal on lines 29 and 74 becomes a high-level voltage signal that sets flip-flop 28 and disables gate 52.

Figure 4:
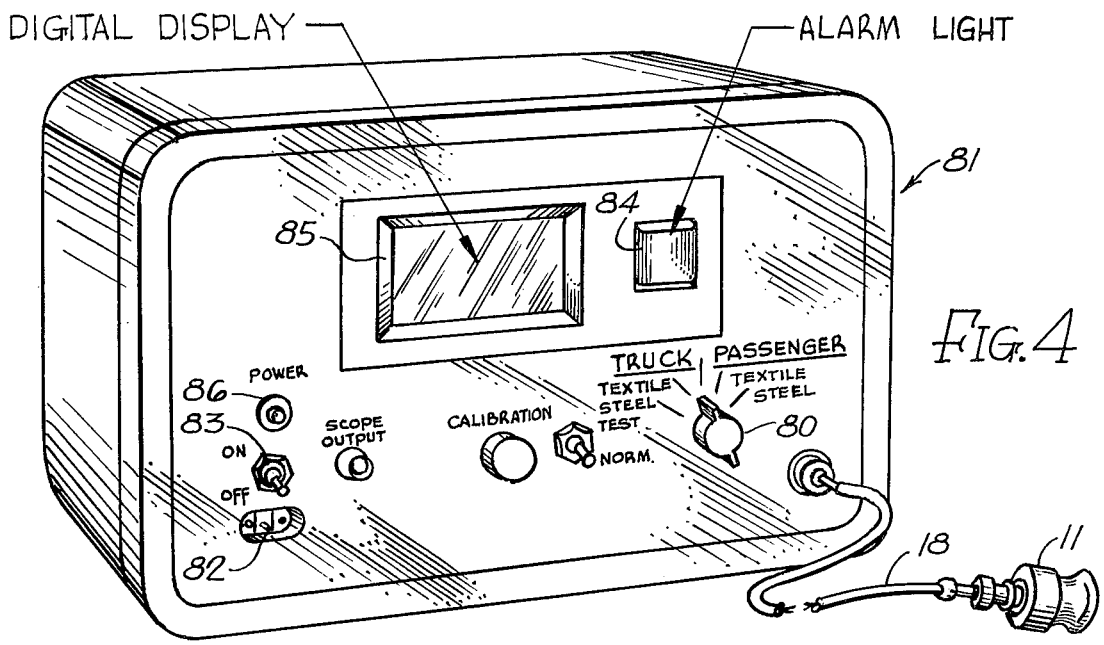
FIG. 4 is a perspective front view of an instrument and the transducer providing the system shown in FIG. 2.

FIG. 4 shows the knob 80 of the rotary switch that is mounted on the front panel of the portable instrument generally indicated at 81 that contains the circuitry, shown on FIG. 2, mounted on printed circuit boards and contains a power supply printed circuit board to provide the various voltages. The power circuit board is connected to a connector 82 and a power switch 83 that are also mounted on the front panel of instrument 81. An alarm light 84 that is a part of defect indicator 39 and a digital display panel 85 of meter 37 are mounted at openings in the front panel of instrument 81. A light 84 is lit when defect indicator 39 is signalled by comparator 34.

Also shown in FIG. 4 are a scope output connector for connecting a cathode ray tube instrument, such as described in said copending patent application. The scope output connector is connected by circuitry connected to line 25 and to line 64 to receive rectified signals and to sum them with the gating signals. A knob for rotation to calibrate the amplifier gain is shown. Also shown is a switch to change to a test mode.

In the normal mode transducer 11 is placed against one end of a cylindrical rubber block that has its other end secured on a cylindrical nylon block. The face of the probe is held flat on the surface of the rubber block. Of course, a film of couplant is placed on the rubber surface before testing. The calibration control is turned back and forth and the digital display should change. Then the calibration control is turned fully clockwise. When this is done the digital display should go off and the red indicator light should turn on. The calibration control is adjusted so a reading of 10 is obtained on the digital display. This is done a number of times to insure consistent readings. This is the case illustratively for the particular construction of the instrument shown in FIG. 4 and having its circuitry shown in FIG. 2.

The foregoing description of preferred embodiments of the system describes the testing of stationary tires. In use it is preferable to place a film of liquid couplant on the tire at the midline along a length, illustratively 18 inches, so that several readings can be obtained by placing the transducer at spaced locations within this 18-inch distance. An average digital value is determined.

The system of the present invention is useful also for inspecting a rotating tire using summing means instead of peak sensing means with the summing means being operated under the control of cyclic control means and with the summing means being a voltage-to-frequency converter and digital counter. The summing means has its output connected to a digital display panel.

The foregoing description has been presented solely for the purpose of illustration and not by way of limitation of the invention because the latter is limited only by the claims that follow.

We claim:
1. A system, useful to predict residual tire life of a steel belted tire, which comprises:
 a band generator having an input and an output to provide pulses of high-frequency electrical energy at said output when triggered by a signal at said input;
 a clock;
 time-delay means that is connected to said clock and to said input of said band generator to provide a trigger signal, after a predetermined delay, to said bang generator for each clock signal;
 a pulse-echo transducer connected to said output of said bang generator to convert received pulses of electrical energy to pulses of ultrasonic energy, to receive ultrasonic energy reflected from plies of a tire when used to examine such tire, and to convert the received reflected ultrasonic energy to signals of electrical energy;
 an amplifier circuit with time varying gain control circuit, said amplifier circuit having an input connected to said bang generator and said transducer and having an output;
 a full-wave rectifier having an output and an input that is connected to said output of said amplifier circuit;
 a gate having an output and an input that is connected to said full-wave rectifier;
 processing means having an output and an input that is connected to said gate, said processing means being constructed to convert the time-gated rectified amplified signals from said output of said gate, after each electrical pulse provided to said transducer, to one voltage signal representing the condition of plies of the casing of the tire;
 means having an input connected to said output of said processing means and constructed to provide a visual readout based on said voltage signal, provided at said output of said processing means that indicates the condition of plies of the casing of the tire; and
 gate-enabling means connected to said gate, to said output of said full-wave rectifier and to said clock, said gate-enabling means being constructed to be responsive to each of said clock signals and after a predetermined delay, greater than said delay of said time-delay means, to process a signal from said rectifier, after said greater delay, that has an amplitude at least equal to that based on the reflected energy from the outer steel belt of the tire, to provide, after a further predetermined delay, an enabling of said gate for a predetermined period of time to pass signals from said rectifier to said processing means.

2. The system of claim 1 wherein:
said processing means is peak sensing means having an output and an input that is connected to said output of said gate; and
said means to provide said visual readout includes a digital panel meter.

3. The system of claim 2 wherein said means to provide a visual readout further includes:
a comparator having an output and an input connected to the output of said peak sensing means, said comparator providing a signal at its output when the voltage signal from said peak sensing means exceeds a predetermined value with reference to a reject reference voltage provided to another input of said comparator; and
a defect indicator including a light, said defect indicator having an input connected to said output of said comparator and constructed to turn on said light when there is a signal at the output of said comparator.

4. The system of claim 3 wherein said digital panel meter has an inhibit input to blank out the operation of said digital panel meter when there is a signal at said inhibit input, said output of said comparator being connected to said inhibit input of said digital panel meter.

5. The system of claim 1 wherein: said gate-enabling means includes:
second time-delay means having an output and an input that is connected to said clock;
gate circuit means having an output, a first input and a second input, said gate circuit means having its said first input connected to said output of said second time-delay means to provide an enable or a disable signal to said gate circuit means from said second time-delay means;
voltage level indicator means having an output connected to said second input of said gate circuit means, a first input connected to said output of said full-wave rectifier and a second input connected to a reference voltage source, that has a value so that voltage signals from said rectifier provide a signal at said output of said indicator means only when the value of that voltage signal from said rectifier is at least about that of the voltage signal due to reflected ultrasonic energy from the outer steel belt of the tire;
flip-flop means having a flip-flop with a set input, a reset input and an output, said reset input being connected to said output of said gate circuit means and said set input being connected to said clock means so that the clock signal from said clock means sets said flip-flop and said gate circuit means resets said flip-flop to provide a signal at its said output, when said output of said gate means, after the time delay period of said second time-delay means, provides a reset signal to said flip-flop whenever there is an output signal from said level indicator means;
third time-delay means having an input connected to said input of said flip-flop and an output connected to said gate, said third time-delay means being constructed to provide at its output after a predetermined delay and then for a predetermined period of time a signal to enable said gate to pass signals from said full-wave rectifier to said processing means,
whereby none of the rectified amplified signals from said full-wave rectifier are provided, for a predetermined period of time, as gated signals to said processing means until after a predetermined period of delay provided by said second time-delay means, after said flip-flop is reset only by the signal based on the reflected ultrasonic energy from the outer steel belt, and then only after a further predetermined delay before said gate is enabled, so that rectified amplified signals to said processing means are signals based on reflected ultrasonic energy from plies other than at least the outer steel belt of the tire.

6. The system of claim 5 wherein said third time-delay means includes first and second monostable multivibrators, each having a trigger input and an output, in which:
said first monostable multivibrator has its trigger input connected to said output of said flip-flop to be triggered by said flip-flop, when said flip-flop is provided with a reset signal, to provide a signal at said output of said monostable multivibrator after a predetermined delay; and
said second monostable multivibrator has its trigger input connected to said output of said first monostable multivibrator to be triggered by the signal from said output of said first monostable multivibrator at the end of its said predetermined period of delay, to provide at said output of said second monostable multivibrator a signal for a predetermined period of time, said output of said second monostable multivibrator being connected to said gate to open said gate for the passage of rectified amplified signals from said rectifier to said processing means for that period of operation of said second monostable multivibrator after it is triggered.

7. The system of claim 6 wherein:
said processing means is peak sensing means having an output and an input that is connected to said output of said gate; and
said means to provide said visual readout includes a digital panel meter.

8. The system of claim 7 wherein said means to provide a visual readout further includes:
a comparator having an output and an input connected to the output of said peak sensing means, said comparator providing a signal at its output when the voltage signal from said peak sensing means exceeds a predetermined value with reference to a reject reference voltage provided to another input of said comparator; and
a defect indicator including a light, said deflect indicator having an input connected to said output of said comparator and constructed to turn on said light when there is a signal at the output of said comparator.

9. The system of claim 8 wherein said digital panel meter has an inhibit input to blank out the operation of said digital panel meter when there is a signal at said inhibit input, said output of said comparator being connected to said inhibit input of said digital panel meter.

10. The system of claim 6 and further including, to be useful also to predict residual tire life of a textile tire, switch means having:
  a first switch with first and second positions having first and second fixed contacts and a moving contact connectable to ground that provide selectively for operation of the system to examine a steel belted tire or a textile tire; and
  second and third switches each with first and second positions having first and second fixed contacts and a moving contact,
  said system having:
  said gate means constructed with third and fourth inputs connected to said first and second fixed contacts, respectively, and connectable to a voltage source, and being constructed:
    to provide, when said first switch is at its first position, a signal from said gate means to said reset input of said flip-flop only when there is a signal at the output of said voltage level indicator means following the signal from said second time-delay means after its delay, to said gate means; and
    to provide, when said first switch is at its second position, a signal from said gate means to said reset input of said flip-flop when there is a signal from said second time-delay means after its delay; and
  said first monostable multivibrator has external timing circuitry including first and second trimmers connected to one terminal of said first multivibrator and connected to said first and second fixed contacts, respectively, of said second switch having its moving contact connected to another terminal of said first multivibrator to complete a circuit between said first and second terminals of said first multivibrator with said first and second trimmers adjusted to provide different timing operations for the two positions of said second switch so that there is a longer period of time before said first multivibrator provides an output signal when said moving contact of said second switch contacts said first fixed contact than when it contacts said second fixed contact of said second switch; and
  said second monostable multivibrator has external timing circuitry including first and second trimmers connected to one terminal of said second multivibrator and connected to said first and second fixed contacts, respectively, of said third switch having its moving contact connected to another terminal of said second multivibrator to complete a circuit between said first and second terminals of said second multivibrator with said first and second trimmers adjusted to provide different timing operations for the two positions of said third switch so that there is a shorter period of time during which said second multivibrator provides an enable output signal to said gate when said moving contact, of said third switch, contacts said first fixed contact than when it contacts said second fixed contact of said third switch.

11. The system of claim 10 wherein said gate means includes:
  a second gate having first and second inputs and an output, said first input of said second gate is the input of said gate means that is connected to said second time-delay means, said second input of said second gate is the third input of said gate means that is connected to said first fixed contact of said first switch;
  a third gate having a first input connected to said output of said second gate, a second input of said second gate that is said second input of said gate means that is connected to said output of said voltage level indicator means, and an output;
  a fourth gate, that is an OR gate, having a first input connected to said output of said third gate, a second input, and an output that is said output of said gate means connected to said reset input of said flip-flop; and
  a fifth gate having an output connected to said second input of said OR gate, a first input that is said first input of said gate means connected to said clock to enable said fifth gate when said clock provides clock signals to said first and second time-delay means, and a second input connected as said fourth input of said gate means that is connected to said second fixed contact of said first switch.

12. The system of claim 11 wherein:
  said processing means is peak sensing means having an output and an input that is connected to said output of said gate; and
  said means to provide said visual readout includes a digital panel meter.

13. The system of claim 12 wherein said means to provide a visual readout further includes:
  a comparator having an output and an input connected to the output of said peak sensing means, said comparator providing a signal at its output when the voltage signal from said peak sensing means exceeds a predetermined value with reference to a reject reference voltage provided to another input of said comparator; and
  a defect indicator including a light, said defect indicator having an input connected to said output of said comparator and constructed to turn on said light when there is a signal at the output of said comparator.

14. The system of claim 13 wherein said digital panel meter has an inhibit input to blank out the operation of said digital panel meter when there is a signal at said inhibit input, said output of said comparator being connected to said inhibit input of said digital panel meter.

15. The system of claim 10, to be useful also to predict residue tire life of a passenger textile tire, wherein:
  said switch means further includes:
    for said first switch a third fixed ontact connected to said first fixed contact of that switch;
    for said second switch a third fixed contact connected to said first fixed contact of that switch; and
    fourth, fifth and sixth switches having first, second and third fixed contacts and a moving contact for each switch, with said first and second fixed contacts for a switch being connected to each other, said moving contact of said fourth switch being connectable to a voltage source and said third fixed contact being connectable to ground,
  said system further including:
  a relay having terminals connected to said bang generator, said transducer and said amplifier circuit in a manner to provide said connection between said amplifier circuit to said bang generator and said transducer, whether said relay is energized or deenergized, said relay having a input connected to said moving contact of said fourth switch so that relay is energized when said first or second fixed contacts of said fourth switch is contacted and is de-energized when said third fixed contact of said fourth switch is contacted;

a RF autotransformer connected to said relay to provide, when said relay is energized to provide by said energized relay said connection between said bang generator and transducer through said autotransformer to said amplifier circuit, an increase in the frequency at which said transducer rings; and amplitude and slope control means having an output connected to said amplifier to change the gain of said amplifier; and first through sixth terminals in which:
said third and sixth terminals are connected to said moving contacts of said fifth and sixth switches, respectively;
said first terminal is connected to said first and second fixed contacts of said fifth switch;
said second terminal is connected to said third fixed contact of said fifth switch;
said fourth terminal is connected to said first and second fixed contacts of said sixth switch; and
said fifth terminal is connected to said third fixed contact of said sixth switch, whereby said fourth through sixth switches when positioned for contact of their moving contacts with fixed contacts 1 and 2 provide no energization of said relay and provide a particular amplitude and slope for the gain provided by said amplifier for testing tires other than said passenger textile tires and when said moving contacts of said fourth through sixth switches when contacting said third fixed contacts provide energization of said relay and provide a greater gain for the amplitude and steeper slope control for said amplifier for testing passenger textile tires.

16. The system of claim 15 wherein said switch means is a rotary switch having a number of decks that provide said first through sixth switches and provides for three positions of said rotary switch a capability of inspection of steel belted tires at one position, truck textile tires at a second position and passenger textile tires at a third position, 17. A method useful to predict residual tire life of a steel belted tire, which comprises:
imparting pulses of ultrasonic energy into an area of steel belted tire in a manner to provide pulses of relected acoustic energy so that each reflected pulse includes reflected ultrasonic energy from plies of the casing of the tire;
converting the pulses of reflected acoustic energy to pulses of electrical signals;
amplifying the electrical signals with time varying gain during each received pulses of electrical signals;
rectifying the amplified electrical signals;
sensing after a predetermined delay, subsequent to said imparting of a pulse of ultrasonic energy, each pulse of rectified amplified electrical signals for the signal representing the reflected ultrasonic energy from the outer steel belt of the tire to provide after a further predetermined delay and then for a predetermined period of time a gating of electrical signals of the pulse;
processing the gated signals of rectified amplified signals to provide information with respect to the amplitude of those gated signals;
determining the difference between that information and information obtainable by the same processing of thus gated rectified amplified signals from an unused, new tire that is of the same type and that has a satisfactory ply construction and has a satisfactory bonding of the cords to the rubber matrix of the tire casing; and
predicting from that difference the extent of circumferential degradation and thus the life of the tire being tested by the system.

18. The method of claim 17 on which the method is performed only a number of times at a small portion of the periphery of a tire.

19. The method of claim 17 in which, in the event that the information obtained from the tire being tested is greater than that obtainable from a satisfactory new, unused tire, the tire is tested at least at a number of areas about the tire to determine that the information is due either to circumferential degradation or to a localized defect.

* * * * *

UNITED STATES PATENT AND TRADEMARK OFFICE
CERTIFICATE OF CORRECTION

PATENT NO. : 4,089,226
DATED : May 16, 1978
INVENTOR(S) : Irvin R. Kraska et al.

It is certified that error appears in the above-identified patent and that said Letters Patent are hereby corrected as shown below:

Column 2, line 3, "degradiation-induced" should read --degradation-induced--.
Column 3, line 13, "timed-gate" should read --time-gated--.
Column 6, line 32, "thread" should read --tread--.
          Lines 34,56 and 64, "$\bar{Q}$" should read --Q--.
Column 9, line 42, "if" should read --in--.
Column 10, line 19, "or" should read --of--.
Column 12, lines 26 and 32, "band" should read --bang--.
Column 13, line 68, "said input" should read --said output--.
Column 16, line 49, "ontact" should read --contact--.
Column 18, line 11, "pulses" should read --pulse--.
          Line 35, "on which" should read --in which--.

Signed and Sealed this

Thirty-first Day of October 1978

[SEAL]

Attest:

RUTH C. MASON
*Attesting Officer*

DONALD W. BANNER
*Commissioner of Patents and Trademarks*